| United States Patent [19] | [11] Patent Number: 4,886,868 |
| Rakoutz, deceased | [45] Date of Patent: Dec. 12, 1989 |

[54] THERMOSETTING COMPOSITION FROM BIS-MALEIMIDE AND N-ALLYL OXY-PHENYL MALEIMIDE

[75] Inventor: Michel Rakoutz, deceased, late of Brignais, France, by Michelle Rakoutz, legal representative

[73] Assignee: Rhone-Poulenc Specialites Chimiques, Courbevoie, France

[21] Appl. No.: 211,276

[22] Filed: Jun. 24, 1988

Related U.S. Application Data

[62] Division of Ser. No. 880,838, Jul. 1, 1986, Pat. No. 4,788,295.

[30] Foreign Application Priority Data

Jul. 1, 1985 [FR] France .................................. 85 10190
Apr. 17, 1986 [FR] France .................................. 86 05744

[51] Int. Cl.$^4$ ........................ C08G 73/12; C08F 22/04
[52] U.S. Cl. ..................... 528/170; 524/261; 524/269; 526/204; 526/262; 528/321; 528/322
[58] Field of Search ....................... 528/322, 321, 170; 526/262, 204; 524/261, 269

[56] References Cited

U.S. PATENT DOCUMENTS

4,788,295 11/1988 Rakoutz .............................. 548/549

Primary Examiner—Harold D. Anderson
Attorney, Agent, or Firm—Burns, Doane, Swecker & Mathis

[57] ABSTRACT

Novel N-(meth)allyloxyphenylmaleimides are prepolymerized with at least one bis-imide and formulated, together with at least one imidazole compound, into thermosetting compositions useful for the production of a wide variety of shaped articles having improved mechanical properties.

16 Claims, No Drawings

THERMOSETTING COMPOSITION FROM BIS-MALEIMIDE AND N-ALLYL OXY-PHENYL MALEIMIDE

This application is a divisional of application Ser. No. 880,838, filed July 1, 1986, now U.S. Pat. No. 4,788,295.

BACKGROUND OF THE INVENTION

1. Field of the Invention:

The present invention relates to novel maleimido compounds and to novel thermosetting compositions comprised thereof, the polymerizates of which have improved mechanical properties.

2. Description of the Prior Art:

N-Substituted maleimides are a known family of chemical compounds and the N,N'-disubstituted bis-maleimides are especially useful for the preparation of thermosetting polymers, the polybis-maleimides.

Monomaleimides are also known to this art. Thus, U.S. Pat. No. 2,444,536 describes a process for the preparation of N-arylmaleimides.

Certain monomaleimides can be used in agrochemisty, as insecticides or fungicides. Others may serve to prepare polymers which can be crosslinked under the influence of light.

Monomaleimides can also be used in mixtures with bis-maleimides for the production of thermosetting polymers.

SUMMARY OF THE INVENTION

A major object of the present invention is the provision of a novel class of monomaleimides having the general formula (I):

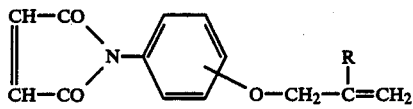

in which R represents a hydrogen atom or a methyl radical.

These novel monomaleimides comprise:
N-(2-allyloxyphenyl)maleimide,
N-(3-allyloxyphenyl)maleimide,
N-(4-allyloxyphenyl)maleimide,
N-(2-methallyloxyphenyl)maleimide,
N-(3-methallyloxyphenyl)maleimide,
N-(4-methallyloxyphenyl)maleimide.

DETAILED DESCRIPTION OF THE PREFERRED EMBODIMENTS OF THE INVENTION

More particularly according to the present invention, the subject maleimides of the formula (I) may be prepared especially from aminophenols (ortho-, meta- or para-), according to the Claisen reaction.

For example, aminophenol, the amino group of which has been previously blocked by reaction with acetic anhydride to form acetamidophenol, may be reacted with an allyl- or a methallyl halide (most frequently, bromide), as the case may be, in solution in acetone and in the presence of dipotassium carbonate. The amino group is later regenerated by hydrolysis.

The corresponding maleimide is then prepared in conventional manner by reacting, in solution, allyloxyaniline or methallyloxyaniline, obtained beforehand, with maleic anhydride in the presence of acetic anhydride, triethylamine and a nickel salt (nickel acetate in particular).

N-Allyloxyphenylmaleimide or N-methallyloxyphenylmaleimide is thus obtained.

N-(4-Allyloxyphenyl)maleimide is a mustard yellow-colored solid having a melting point of approximately 103° C.

The NMR results reflect the following structure:

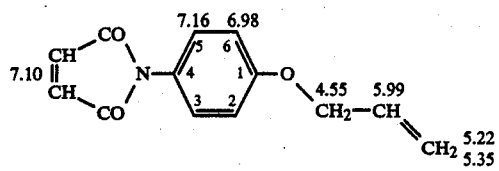

NMR 1H; solvent: DMSO d6; reference: hexamethyldisiloxane (HMDS) δ7.16 (2H,m): H 3,5; δ7.10 (2H,s): maleimido; δ6,98 (2H,m): H 2,6; δ5.99 (1H,m): —H=; δ5.35 and 5.22 (2H,dd): =CH2; δ4.55 (2H,d): OCH2.

N-(3-Allyloxyphenyl)maleimide is a viscous orange-yellow liquid, which crystallizes slowly at room temperature and boils at approximately 150° C. at a pressure of 20 Pa.

The NMR results reflect the following structure:

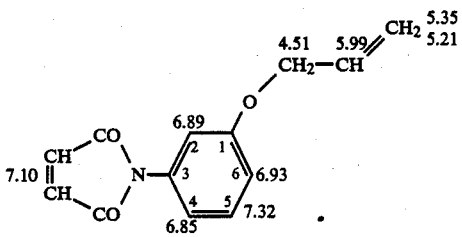

NMR 1H; solvent: DMSO d6; reference: HMDS δ6.85, 6.89 and 6.93 (3H,m): H4, H2 and H6; δ7.10 (2H,s): maleimido; δ7.32 (1H,5): H5; δ5.99 (1H,m): —CH=; δ5.35 and 5.21 (2H,dd): =CH2; δ4.51 (2H,d): OCH2.

N-(2-Allyloxyphenyl)maleimide is a pale yellow crystalline solid, having a melting point of approximately 82° C. and a boiling point of 148° C. to 155° C. at a pressure of 20 Pa.

The NMR results reflect the following structure:

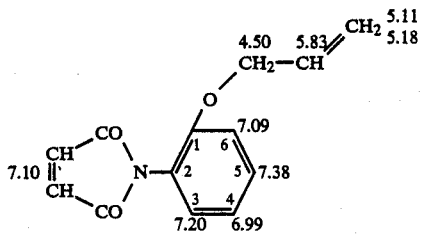

NMR 1H; solvent: DMSO d6; reference: HMDS δ7.38 (2H,dt): H5; δ7.20 (1H,dd): H3; δ7.15 (2H,d): maleimido; δ7.09 (1H,dd): H6; δ6.99 (1H,dt): H4; δ5.83 (1H,m): —CH=; δ5.18 and 5.11 (2H,dd): =CH2; δ4.50 (2H,d): OCH2.

N-(4-Methallyloxyphenyl)maleimide is a beigecolored solid having a melting point of 64° C.

The NMR results reflect the following structure:

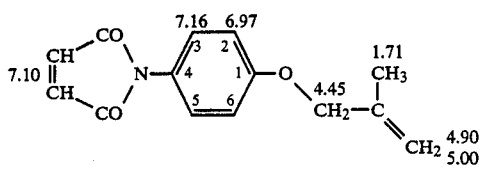

NMR 1H; solvent: DMSO d6; reference: HMDS δ7.16 (2H,d): H 3,5; δ7.09 (2H,s): maleimido; δ6.97 (2H,d): H 2,6; δ4.90 and 5.00 (1H,s): CH₂=; δ4.45 (2H,s): OCH₂ ; δ1.71 (3H,s): CH₃.

N-(3-Methallyloxyphenyl)maleimide is a beige-colored solid having a melting point of 39° C.

The NMR results reflect the following structure:

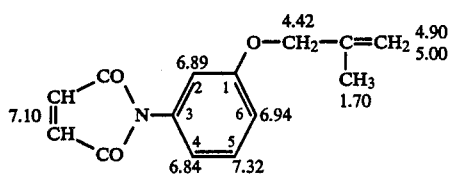

NMR 1H; solvent: DMSO d6; reference: HMDS δ7.32 (1H,t): H5; δ7.10 (2H,2): maleimido; δ6.94 (1H,d): H6; δ6.89 (1H,s): H2; δ6.84 (1H,d): H4; δ4.90 and 5.00 (1H,1): CH₂=; δ4.42 (2H,s): OCH₂ ; δ1.70 (3H,s): CH₃

N-(2-Methallyloxyphenyl)maleimide is a beige-colored solid having a melting point of 96° C.

The NMR results reflect the following structure:

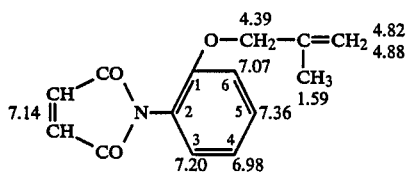

NMR 1H; solvent: DMSO d6; reference: HMDS δ7.36 (1H,t): H5; δ7.20 (1H,d): H3; δ7.14 (2H,s): maleimido; δ7.07 (1H,d): H6; δ6.98 (1H,t): H4; δ4.82 and 4.88 (1H,s): CH₂=; δ4.39 (2H,2): OCH₂; δ1.59 (3H,s): CH₃ .

The novel monomaleimides of the general formula (I), when they are used with one or more bis-maleimides to prepare thermosetting compositions for molding or for impregnation, impart to such compositions improved mechanical properties compared with compositions which have been prepared without these novel monomaleimides.

More precisely, the present invention also features novel thermosetting compositions, characterized in that they are comprised of:

(A) a prepolymer obtained by reaction between 50° C. and 300° C. of:

(a) a bis-imide or a combination of several bis-imides of the general formula (II):

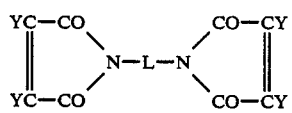

in which:

Y represents a hydrogen atom or a methyl group;

L represents a divalent hydrocarbon radical, such as a cyclohexylene radical; a phenylene radical; the 4-methyl-1,3-phenylene radical; the 2-methyl-1,3-phenyl radical; the 5-methyl-1,3-phenylene radical; the 2,5-diethyl-3-methyl-1,4-phenylene radical: and the radicals of the formula (III):

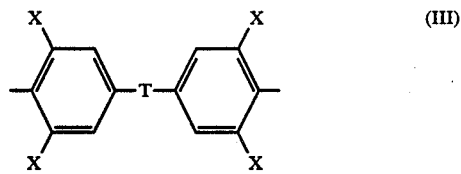

in which:

T represents a simple valency bond or one of the following atoms or groups;

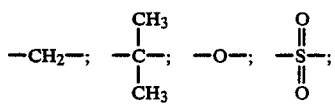

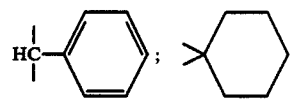

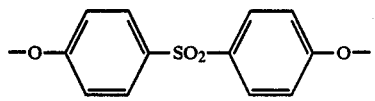

X represents a hydrogen atom, a methyl, ethyl or isopropyl radical; with (b) one or more monomaleimides of the general formula (I):

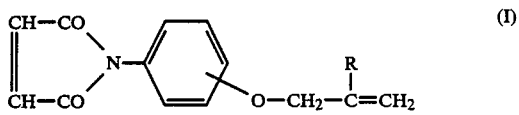

in which R represents a hydrogen atom or a methyl radical; and, if appropriate, with (c) an organosilicic compound containing at least one hydroxyl group bonded to a silicon atom in its molecule; and (B) imidazole or an imidazole derivative.

Exemplary of the bis-maleimides of the formula (II), representative are:

N,N'-meta-phenylene-bis-maleimide;
N,N'-para-phenylene-bis-maleimide;
N,N'-4,4'-diphenylmethane-bis-maleimide;
N,N'-4,4'-diphenylether-bis-maleimide;
N,N'-4,4'-diphenylsulfone-bis-maleimide;
N,N'-1,4-cyclohexylene-bis-maleimide;
N,N'-4,4'-(1,1-diphenylcyclohexylidene)-bismaleimide;
N,N'-4,4'-(2,2-diphenylpropane)bis-maleimide;
N,N'-4,4'-triphenylmethane-bis-maleimide;
N,N'-1,3-(4-methylphenylene)bis-maleimide;
N,N'-1,3-(2-methylphenylene)bis-maleimide.

Among these bis-maleimides, particularly preferred are N,N'-4,4'-diphenylmethane-bis-maleimide, N,N'-

1,3-(4-methylphenylene)bis-maleimide, N,N'-1,3-(2-methylphenylene)bis-maleimide, and mixtures thereof.

These bis-maleimides can be prepared according to the processes described in U.S. Pat. No. 3,018,290 and British Patent No. 1,137,290.

The monomaleimide of the general formula (I) is preferably:
N-(2-allyloxyphenyl)maleimide;
N-(3-allyloxyphenyl)maleimide;
N-(4-allyloxyphenyl)maleimide;
N-(2-methallyloxyphenyl)maleimide;
N-(3-methallyloxyphenyl)maleimide;
N-(3-methallyloxyphenyl)maleimide;
and mixtures thereof.

The hydroxylated organosilicic compounds, which optionally comprise the subject compositions, are known compounds of the following general formula (IV):

$$\text{HO}\left[\begin{array}{c}R_1\\|\\ \text{Si}-\text{O}\\|\\ R_2\end{array}\right]_y \begin{array}{c}R_3\\|\\ \text{Si}-R_5\\|\\ R_4\end{array}$$

in which $R_1$, $R_2$, $R_3$, $R_4$ and $R_5$, which may be identical or different, represent:
(i) a hydroxyl group or a group of the type $-OR_6$ in which $R_6$ may be a straight or branched chain alkyl radical containing 1 to 6 carbon atoms or a phenyl radical;
(ii) a hydrogen atom;
(iii) a straight or branched chain alkyl radical containing 1 to 6 carbon atoms which may be optionally substituted with one or more chlorine or fluorine atoms or with a $-CN$ group;
(iv) a straight or branched chain alkenyl radical containing 2 to 6 carbon atoms;
(v) a phenyl radical, optionally substituted with one or more alkyl and/or alkoxy radicals containing 1 to 4 carbon atoms, or with one or more chlorine atoms; and y is an integer or a fractional number from 0 to 1000.

For an organosilicic compound defined by formula (IV), y is, in fact, always an integer, but as in this case compounds having a polymeric structure (when y is greater than 1) are concerned, it is rare that a single compound is obtained, but most frequently a mixture of compounds of the same chemical structure, which differ by the number of recurring units in their molecule is obtained; this leads to a mean value for y, which may be an integer or a fractional number.

The hydroxylated organosilicic compounds of the type mentioned above can be characterized by the ratio of the weight of the hydroxyl groups they contain to the total weight of their molecule.

The use of a hydroxylated organosilicic compound is a measure which especially facilitates, during the preparation of the thermosetting compositions according to the present invention, the transition of the compounds with maleimide groups to the molten state and it also makes it possible to impart a greater fluidity to the thermosetting resin in the molten state.

When the organosilicic compounds in fact are present, the compounds which are preferred are those mentioned above in which the ratio by weight of the hydroxyl groups in the molecule is at least 0.05% and preferably 0.1%.

Among the organosilicic compounds of this preferred group, those which are particularly well suited are the compounds of the formula (IV) in which:
$R_1$, $R_2$, $R_3$ and $R_4$, which may be identical or different, represent a straight or branched chain alkyl radical containing 1 to 6 carbon atoms or a straight or branched chain alkenyl radical containing 2 to 6 carbon atoms or a phenyl radical;
$R_5$ represents a hydroxyl group; and
y is an integer or a fractional number, from 0 to 250.

This circumscribes, therefore, silane-diols when y is 0 or, polysiloxane-diols when y is other than 0.

For the preparation thereof, see W. NOLL: *Chemistry and Technology of Silicones* (English translation of the German edition of 1968), published by Academic Press of New York.

The organosilicic compound which are particularly suitable are:
diethylsilane-diol;
diphenylsilane-diol;
methylphenylsilane-diol;
1,1,3,3-tetramethyldisiloxane-1,3-diol;
1,1-dimethyl-3,3-diphenyldisiloxane-1,3-diol;
1,3-dimethyl-1,3-diphenyldisiloxane-1,3-diol;
1,1,3,3,5,5-hexamethyltrisiloxane-1,5-diol;
1,1,3,3,5,5,7,7-octamethyltetrasiloxane-1,7-diol;
1,1,3,3,5,5,7,7,9,9-decamethylpentasiloxane-1,9-diol;
1,1,3,3,5,5,7,7,9,9,11,11-dodecamethylhexasiloxane1,11-diol;
1,3,5,7,9-pentamethyl-1,3,5,7,9-pentaphenylpentasiloxane-1,9-diol;
and the corresponding higher members of the series.

The hydroxylated organosilicic compounds which are especially well suited may also be mixtures of two or more of the compounds mentioned above. Thus, commercially available hydroxylated polysiloxane oils or resins may be used for convenience. These are, especially, $\alpha,\omega$-dihydroxylated polymethylpolysiloxane oils containing from 0.2 to 0.3% by weight of hydroxyl groups (Rhone-Poulenc 48 V 500 oil), or 10 to 12% by weight of hydroxyl groups (Rhone-Poulenc 48 V 50 oil) or $\alpha,\omega$-dihydroxylated methylphenylpolysiloxane oils or resins containing 4.5% to 5% by weight of hydroxyl groups (Rhone-Poulence oil 5-606) or from 7.5 to 8.5% by weight of hydroxyl groups (Rhône-Poulenc resin 50305); these commercially available oils or resins are given by way of example, but there are others which may be just as suitable.

In the prepolymers (A) prepared from one or more bis-imides of formula (II) and from one or more monomaleimides of formula (I), the amounts of reagents are selected such as to obtain, by weight in relation to the total weight of these different constituents:
from 50 to 95% of bis-imide(s), and
from 5 to 50% monomaleimide(s).

In the prepolymers (A) prepared from one or more bis-imides of formula (II), from one or more monomaleimides of formula (I) and a hydroxylated organosilicic compound of formula (IV), the amounts of reagents are selected such as to obtain, by weight in relation to the total weight of these different constituents:
from 40 to 90% of bis-imide(s),
from 5 to 40% of monomaleimide(s), and
from 5 to 40% of the hydroxylated organosilicic compound.

To obtain compositions according to the invention of this type which have superior flexural properties when heated, it is preferable to use a proportion of the organosilicic compound of 5 to 20% (by weight) of the total weight of bis-imide(s), monomaleimide(s) and the hydroxylated organosilicic compound.

The imidazole derivative (B) advantageously has the general formula (V):

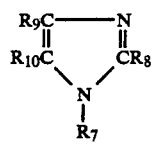

in which $R_7$, $R_8$, $R_9$ and $R_{10}$, which may be identical or different, represent: a hydrogen atom, an alkyl or alkoxy radical containing 1 to 20 carbon atoms, a vinyl radical, a phenyl radical, a nitro group, $R_9$ being capable of forming with $R_{10}$ and the carbon atoms to which these radicals are linked, a single ring such as, for example, a benzene ring, $R_7$ may also represent a carbonyl group linked to a second imidazole ring.

As specific examples of such imidazole derivatives, representative are imidazole or glyoxaline, 1-methylimidazole, 2-methylimidazole, 1,2-dimethylimidazole, 1-vinylimidazole, 1-vinyl-2-methylimidazole, benzimidazole and carbonyldiimidazole.

The imidazole derivative is used in catalytic quantities. According to the nature of the imidazole derivative and according to the rate of polymerization desired at the time of use, the imidazole derivative is used at a proportion of between 0.02 and 1% by weight relative to the prepolymer (A).

An imidazole proportion of 0.05 to 0.5% by weight relative to the prepolymer (A) is preferably used.

The compositions according to the invention may also contain a N,N′,N″-tris(hydroxyalkyl)hexahydrotriazine; N,N′,N″-tris(hydroxyethyl)hexahydro-1,3,5-triazine, N,N′,N″-tris(hydroxypropyl)hexahydro-1,3,5-triazine and N,N′,N″-tris(hydroxybutyl)hexahydro-1,3,5-triazine are the preferred.

N,N′,N″-Tris(hydroxyethyl)hexahydro-1,3,5-triazine, which is commercially available, is preferably used.

N,N′,N″-Tris(hydroxyalkyl)hexahydrotriazine, when it is present, confers on the thermosetting compositions a higher viscosity and an improvement of the thermomechanical properties, especially of flexural strength.

From 0 to 5% by weight of N,N′,N″-tris(hydroxyalkyl)hexahydrotriazine relative to the prepolymer (A) is typically used.

To obtain a good efficiency, it is preferable to use from 0.5 to 2% by weight of N,N′,N″-tris(hydroxyalkyl)hexahydrotriazine relative to the prepolymer (A).

The compositions according to the invention, after heat treatment, provide mechanical properties, especially flexural, at ambient temperature and on heating (usually 250° C.) which are superior to those obtained with prior compositions, such as those described in French Patent Application No. 83/17,218, published under No. 2,553,780.

Various adjuvants may also be incorporated into the compositions according to the invention. These adjuvants which are commonly used and are well known to those skilled in this art may be, for example, stabilizers or degradation inhibitors, lubricants or stripping agents, colorants or pigments, powdery or particle fillers such as silicates, carbonates, kaolin, chalk, ground quartz, mica or glass microbeads, etc. Adjuvants which modify the physical structure of the product obtained such as, for example, porogenous agents or fibrous reinforcing agents: fibrils of carbon, polyimide, aromatic polyamides, whiskers, etc. may also be incorporated.

The manufacturing process is such that the thermosetting resin which is ready for use is sufficiently supple and sticky in a thin layer. Additionally, to obtain a homogeneous material after lamination, reactions which give rise to highly volatile compounds at the treatment temperatures should be limited. To this end, when the initial reagents contain a silanediol, it is desirable to first carry out the major part of the oligomerization reaction yielding water as by-product; this water can be removed more easily during the course of the manufacture of the resin.

Firstly, an intimate mixing of the compounds with the maleimide groups and, if appropriate, the hydroxylated organosilicic compound is carried out. In order to avoid a premature homopolymerization of maleimides which would give rise to a resin which is too viscous, the maleimides+(if appropriate) hydroxylated organosilicic compound mixture is melted in the absence of a catalyst at a temperature not exceeding the melting point of the most difficult maleimide to liquefy. If the reaction mixture contains an organosilicic compound with a high content of hydroxyl groups, the mixture is, in this case, maintained in the molten state such as to carry out a part of the oligomerization of the silanediol; preferably, this compound is heated to about 150° C. until approximately 40% of the initial hydroxyl groups have disappeared during the oligomerization of this compound. In another embodiment, this oligomerization could be carried out before the introduction of the compounds having maleimide groups.

The imidazole derivative (B) and the N,N′,N″-tris(hydroxyalkyl)hexahydrotriazine where appropriate, are then added to the mixture which is well stirred, such as to enable their rapid dispersion.

When the catalyst is particularly active, it is desirable to add it with a solvent which is compatible with the reaction medium in order to avoid its encapsulation in the polymer network which it generates. Thus, a solvent such as triallyl isocyanurate, diallyl phthalate or allyl benzoate can be used.

A volatile solvent which will be eliminated later by evaporation under reduced pressure can also be used. In fact, the mixture is degassed to eliminate volatile products which are undesirable for the preparation of the laminates. The mixture is cast immediately after homogenization.

The thermosetting compositions according to the invention have a sufficient pegosity for applications such as laminates and composite materials.

The compositions can be used in molding or impregnation procedures. They can be used for the production of coatings, gluings, laminates and reinforced composite materials. The reinforcing material can be in the form of woven or unwoven sheets, of unidirectional elements or of natural or synthetic cut fibers such as filaments or fibers of glass, boron, carbon, tungsten, silicon, polyamide-imides or aromatic polyamides. The compositions are of special value in obtaining intermediate articles which are preimpregnated without a solvent. The impregnation of the fibrous material may be carried out using common techniques such as dip-coating, coating with a doctor blade or with curtain or impregnation by transfer. The transferable film and the preimpregnated articles may be used directly or stored for later use; they retain their properties very satisfactorily during a cold storage between 0° and 10° C.

The impregnated materials can be used for making parts of various shapes and uses in numerous industries, such as, for example, in aeronautics. These parts, which may be revolving parts, are obtained by placing several layers of prepregs on a shape or a support.

Crosslinking is then carried out under the usual technological conditions relating to composite materials, and, in particular, at temperatures of from 100 to 300° C.

The prepegs can also be used as reinforcements or as means for repairing deteriorated parts.

However, it is also possible to produce parts according to the techniques of filament winding, with or without support, or by injection molding, or by pultrusion.

Thus, shaped products having high mechanical and thermal resistance may facilely be obtained.

In order to further illustrate the present invention and the advantages thereof, the following specific examples are given, it being understood that same are intended only as illustrative and in nowise limitative.

EXAMPLE 1

Preparation of N-(4-allyloxyphenyl)maleimide:

The title compound was prepared from para-allyloxyaniline, a suitable procedure for the preparation of which is featured in *J.A.C.S.*, 44, pp. 1741–44 (1922).

Into a glass reactor, equipped with a central stirrer, a thermometer and an ascending coolant, maintained at 50° C. under stirring and in which a slow stream of nitrogen was circulated:

(i) 249 g of an acetone solution containing 149.0 g of para-allyloxyaniline; and (ii) 249 g of an acetone solution containing 112.7 g of maleic anhydride;

were simultaneously introduced over the course of 20 minutes, by means of two dropping funnels.

The reaction was exothermic and gave the immediate formation of a yellowish suspension.

When the additions were complete, each funnel was rinsed with acetone (10 cc), the contents of each of which were then added to the reaction mass, still maintained under stirring.

The dropping funnel which previously contained the maleic anhydride, was charged with 163.2 of acetic anhydride and the other funnel was charged with 45.4 g of triethylamine.

These two compounds were then introduced into the reactor over the course of 5 minutes and an aqueous solution (1.9 cc) containing 0.0528 mole of nickel acetate per 100 cc of solution was then added thereto.

The reaction mixture was maintained at the reflux temperature, under stirring, for 2 hr, 30 min. The temperature was then decreased to 30° C., 1349 g of distilled water were added and the mixture was then cooled to 15° C. under stirring.

The dark yellow precipitate was drained, washed with an 80:20 (v/v) mixture of acetone:water (100 cc), which had previously been cooled to 10° C., and then with distilled water (100 cc).

The drained solid was dried for 15 hr at 40° C. under reduced pressure (30 Pa).

215.5 g of a powdery material having a mustard yellow color and an m.p. of 103° C. were thus obtained.

The NMR spectrum corresponded to the structure of N-(4-allyloxyphenyl)maleimide.

EXAMPLE 2

Preparation of N-(3-allyloxyphenyl)maleimide:

The same apparatus as in Example 1 was used and the same procedure was followed.

The starting material was meta-allyloxyaniline, a procedure for the preparation of which is described in *Chemical Abstracts*, 51, 4423 a to g (1957).

The amounts used very twice those used in Example 1:

(i) 498 g of an acetone solution containing 298.0 g of meta-allyloxyaniline;

(ii) 498 g of an acetone solution containing 225.4 g of maleic anhydride;

(iii) rinsing of each dropping funnel with acetone (20 cc);

(iv) 326.4 g of acetic anhydride;

(v) 90.8 g of triethylamine;

(vi) an aqueous solution (3.8 cc) containing 0.0528 mole of nickel acetate per 100 cc of solution; and (vii) 2698 g of distilled water.

The addition of 2698 g of distilled water to the reaction mixture resulted in the settling of a dark-colored oil, which was extracted with ethyl acetate (3×250 cc). The organic layers obtained were combined and dried over sodium sulfate.

After removal of the solvent by drying under reduced pressure (initially at about 3000 Pa, and then at about 70 Pa), 464 g of a very dark, thick oil containing 0.309 ethylene double bonding per 100 g were obtained.

22.77 g of this crude product were taken and 0.2 g of hydroquinone was added. This was distilled at a pressure of 12 Pa, in a 50 cc reactor equipped with a Vigreux column and with a fraction separator.

14.7 g of a fraction distilling between 150° C. and 155° C. at 20 Pa were collected.

This was a clear, orange-yellow, viscous liquid with an NMR spectrum which corresponded to the structure of N-(3-allyloxyphenyl)maleimide.

EXAMPLE 3

Preparation of N-(2-allyloxyphenyl)maleimide:

This compound was prepared from 2-allyloxyaniline itself prepared as in *J.A.C.S.*, 70, PAGE 593 (1948).

Into a glass reactor equipped with a central stirrer, a thermometer and an ascending coolant, maintained at 50° C. under stirring and in which a slow stream of nitrogen was circulated:

(i) an acetone solution (443 cc) containing 298 g of 2-allyloxyaniline; and (ii) an acetone solution (443 cc) containing 235.2 g of maleic anhydride; were introduced simultaneously over the course of 30 minutes, by means of 2 dropping funnels.

The reaction was exothermic and gave the immediate formation of a yellowish suspension.

When the additions were complete, each funnel was rinsed with acetone (10 cc), the contents of each of which were then added to the reaction mass, still maintained under stirring.

The funnel which previously contained the maleic anhydride was charged with 265.2 g of acetic anhydride, and the other funnel was charged with 60.6 g of triethylamine.

These two compounds were then introduced into the reactor over the course of 6 minutes and an aqueous solution (3.8 cc) containing 0.0528 mole of nickel acetate per 100 cc of solution was then added thereto.

The reaction mixture was maintained at the reflux temperature, under stirring, for 2 hr, 30 minutes. The temperature was then decreased to 30° C., 2500 g of distilled water were added and the mixture was then cooled to 20° C. under stirring.

A dark oil rose to the surface of the aqueous phase. The aqueous phase was siphoned off and the oily phase was taken up with ethyl acetate (400 cc). The organic phase was washed with distilled water (2×500 cc) until the pH of the water used for washing was equal to 6. The organic phase which was separated by decantation was dried over 150 g of anhydrous sodium sulfate.

After removal of the solvent by drying under reduced pressure (initially at about 3000 Pa, then at about 70 Pa), 450 g of a very dark thick oil were obtained; this was treated with ethyl alcohol (560 cc), the mixture was cooled to 5° C. in ice, and filtered. 416 g of a moist beige-colored precipitate were obtained. This was dried for 15 hours at 40° C. under reduced pressure 930 Pa and 365 g of a beige-colored crystalline material having a m.p. of 82° C. were obtained.

The NMR spectrum corresponded to the structure of N-(2-allyloxyphenyl)maleimide.

EXAMPLE 4

Preparation of N-(4-methallyloxyphenyl)maleimide:

This compound was prepared from 4-methallyloxyaniline.

(4.1) 4-methallyloxyaniline:

This compound was prepared from para-methallyloxyacetamidobenzene. The latter compound was obtained by a method analogous to that for the preparation of orthoacetamidophenylallyl ether, described in *J.A.C.S.*, 70, page 593 (1948), substituting the allyl bromide with methallyl chloride, and operating in the presence of a catalytic amount of potassium iodide (10% in moles relative to methallyl chloride).

Into a glass reactor equipped with a central stirrer, a thermometer and an ascending coolant;

(i) 205 g of para-methallyloxyacetamidobenzene; and
(ii) 5N ethanolic sodium hydroxide (400 cc); were added. After homogenization;

13.6 g of imidazole, which was 20% (in moles) relative to the para-methallyloxyacetamidobenzene, were added.

The reaction mixture was maintained at the reflux temperature, under stirring, for 3 hours.

The reaction mixture was cooled to 20° C.

The ethanol was removed under reduced pressure (about 70 Pa).

Ethyl acetate (250 cc) was added to the reaction mass, and the mixture was washed with distilled water (2 x 250 cc) until the washings attained a pH of 7.

The ethyl acetate in the organic phase was removed under reduced pressure (about 70 Pa) and 165.5 g of the crude product were obtained.

135.4 g of the purified product were obtained by distillation at 113° C. at 0.05 mm Hg.

The NMR spectrum corresponded to the structure of 4-methallyloxyaniline.

(4.2) N-(4-methallyloxyphenyl)maleimide:

Into a glass reactor equipped with a central stirrer, a thermometer and an ascending coolant, maintained at 50° C., under stirring, and in which a slow stream of nitrogen was circulated:

(i) an acetone solution (52 cc) containing 32.6 g of 4-methallyloxyaniline; and
(ii) an acetone solution (52 cc) containing 22.5 g of maleic anhydride; were simultaneously introduced over the course of 15 minutes by means of two dropping funnels.

The reaction was exothermic and gave the immediate formation of a yellowish suspension.

When the additions were complete, each funnel was rinsed with acetone (10 cc), the contents of each of which were then added to the reaction mass, still maintained under stirring.

The dropping funnel which previously contained the maleic anhydride was charged with 26.5 of acetic anhydride and the other funnel was charged with 6.1 g of triethylamine.

These two compounds were then introduced into the reactor over the course of 5 minutes and an aqueous solution (0.4 cc) containing 0.0528 mole of nickel acetate per 100 cc of solution was then added.

The reaction mixture was maintained at the reflux temperature, under stirring, for 2 hours, 30 minutes. The temperature was then decreased to 20° C.

The reaction mixture was precipitated by pouring it slowly into iced water (500 cc), under vigorous stirring.

The precipitate was filtered, washed again with cooled distilled water, and dried for 15 hours at 40° C. under reduced pressure (30 Pa). 39.4 g of a beige-colored precipitate, having an m.p. of 64° C. were obtained.

The NMR spectrum corresponded to the structure of N-(4-methallyloxyphenyl)maleimide.

EXAMPLE 5

Preparation of N-(3-methallyloxyphenyl)maleimide:

(5.1) 3-methallyloxyaniline:

The starting material was meta-methallyloxyacetamidobenzene, which was obtained under the same conditions as those described in Example 4, paragraph (4.1) for paramethallyloxyacetamidobenzene.

Into a glass reactor equipped with a central stirrier, a thermometer and an ascending coolant:

(i) 205 g of meta-methallyloxyacetamidobenzene; and
(ii) 5N ethanolic sodium hydroxide (400 ml); were introduced.

After homogenization:

13.6 g of imidazole, which was 20% (in moles) were added.

The reaction mixture was maintained at the reflux temperature, under stirring, for 3 hours.

The reaction mixture was cooled to 20° C.

The ethanol was removed under reduced pressure (about 70 Pa).

Ethyl acetate (250 cc) was added to the reaction mass, and the mixture was washed with distilled water (2×250 cc) until the washings attained a pH of 7.

The ethyl acetate in the organic phase was removed under reduced pressure (about 70 Pa) and 144 g of the crude product were obtained.

124 g of the purified material were obtained by distillation at 85° C. at 0.05 mm Hg.

The NMR spectrum corresponded to the structure of 3-methallyloxyaniline.

(5.2) N-(3-methallyloxyphenyl)maleimide:

Into a glass reactor equipped with a central stirrer, a thermometer and an ascending coolant maintained at 50° C., under stirring, and in which a slow stream of nitrogen was circulated;

(i) an acetone solution (105 cc) containing 65.2 g of 3-methallyloxyaniline; and (ii) an acetone solution (105 cc) containing 45.0 g of maleic anhydride;

were introduced simultaneously over the course of 20 minutes by means of two dropping funnels.

The reaction was exothermic and gave the immediate formation of a yellowish suspension.

When the additions were complete, each funnel was rinsed with acetone (10 cc), the contents of each of which were then added to the reaction mass, still maintained under stirring.

The dropping funnel which previously contained the maleic anhydride was charged with 53.0 g of acetic anhydride and the other funnel was charged with 12.2 g of triethylamine.

These two compounds were then introduced into the reactor over 5 minutes and an aqueous solution (0.8 cc) containing 0.0528 mole of nickel acetate per 100 cc of solution was then added.

The reaction mixture was maintained at the reflux temperature, under stirring, for 2 hours, 30 minutes. The temperature was then decreased to 20° C.

The reaction mixture was precipitated in distilled water at 10° C. (500 cc). The viscous, very dark oil collected was washed with a pH 7 phosphate buffer (250 cc), then with distilled water (2×500 cc). The product obtained by drying under reduced pressure (30 Pa) for 15 hours at 30° C. was cooled in an acetone +solid carbon dioxide mixture; 78 g of a beige-colored solid having an m.p. of 39° C. were thus obtained.

The NMR spectrum corresponded to the structure of N-(3-methallyloxyphenyl)maleimide.

EXAMPLE 6

Preparation of N-(2-methallyloxyphenyl)maleimide:

This compound was prepared from 2-methallyloxyaniline.

(6.1) 2-methallyloxyaniline:

The starting material was ortho-methallyloxyacetamidobenzene, which was obtained under the same conditions as those described in Example 4, paragraph (4.1), for paramethallyloxyacetamidobenzene.

Into a glass reactor equipped with a central stirrer, a thermometer and an ascending coolant;

(i) 205 g of ortho-methallyloxyacetamidobenzene; and (ii) 5N ethanolic sodium hydroxide (400 ml); were introduced. After homogenization:

13.6 g of imidazole, which was 20% (in moles) were added.

The reaction mixture was maintained at the reflux temperature, under stirring, for 3 hours.

The reaction mixture was cooled to 20° C.

The ethanol was removed under reduced pressure (about 70 Pa).

Ethyl acetate (250 cc) was added to the reaction mass and the mixture was washed with distilled water (2×250 cc) until the washings attained a pH of 7.

The ethyl acetate was removed from the organic phase under reduced pressure (about 70Pa) and 168.10 g of crude product were obtained. 136.10 g of the purified product were obtained by distillation at 81° C. at 0.05 mm Hg.

The NMR spectrum corresponded to the structure of 2-methallyloxyaniline.

(6.2) N-(2-methallyloxyphenyl)maleimide:

Into a glass reactor equipped with a central stirrer, a thermometer and an ascending coolant maintained at 50° C., under stirring, and in which a slow stream of nitrogen was circulated:

(i) an acetone solution (105 cc) containing 65.2 g of 2-methallyloxyaniline: and (ii) an acetone solution (105 cc) containing 45.0 g of maleic anhydride;

were simultaneously introduced, over the course of 20 minutes, by means of 2 dropping funnels.

The reaction was exothermic and gave the immediate formation of a yellowish suspension.

When the additions were complete, each funnel was rinsed with acetone (10 cc), the contents of each of which were then added to the reaction mass, still maintained under stirring.

The dropping funnel which previously contained the maleic anhydride was charged with 53.0 g of acetic anhydride and the other funnel was charged with 12.2 of triethylamine.

These two compounds were then introduced into the reactor over the course of 5 minutes and an aqueous solution (0.8 cc) containing 0.0528 mole of nickel acetate per 100 cc of solution was then added.

The reaction mixture was maintained at the reflux temperature, under stirring, for 2 hours, 30 minutes. The temperature was then decreased to 20° C.

The reaction mixture was precipitated in iced distilled water (500 cc) under vigorous stirring. The chestnut-colored precipitate was filtered, washed again with cooled distilled water, and dried for 15 hours at 40° C. under reduced pressure (30 Pa), and 70.0 g of a beige-colored precipitate having an m.p. of 96° C. were obtained.

The NMR spectrum corresponded to the structures of N-(2-methallyloxyphenyl)maleimide.

EXAMPLE 7

An apparatus which consisted of a glass reactor equipped with a central stirrer and a degassing tubulus connected to a vacuum pump through cold traps (acetone +solid carbon dioxide mixture) was used.

The reactor containing 17.78 g of N-(3-allyloxyphenyl)maleimide was placed in an oil bath heated to 150° C. After 3 minutes of heating, 60.44 g of N,N'-4,4'-diphenylmethane-bis-maleimide were charged therein, over the course of 3 minutes, under stirring. After 2 minutes, the reaction mass was degassed under reduced pressure (1330 Pa) for 10 minutes at 150° C. The reaction mass was then clear and it cooled to 130° C. in 4 minutes.

Atmospheric pressure was re-established in the reactor and a solution based on 0.09 g of imidazole and 1.69 g of triallyl isocyanurate was introduced.

The mixture was stirred briefly, while maintaining the temperature at 130° C.; it was then degassed again under reduced pressure (1330 Pa) for 3 minutes.

Atmospheric pressure was re-established in the reactor and the resin contained therein was then cast in a mold which was pre-heated to 120° C. and made of two rectangular chromium-plated plates which were separated by a 4 mm-thick air gap.

The crosslinking of the resin contained in the mold was carried out at atmospheric pressure in an oven heated according to the thermal cycle below:

(a) temperature rise from 120° C. to 150° C. in 1 hour;
(b) maintenance at 150° C. for 1 hour;
(c) temperature rise from 150° C. to 200° C. in 40 minutes;
(d) maintenance at 200° C. for 2 hours;
(e) temperature rise from 200° C. to 250° C. in 40 minutes;
(f) maintenance at 250° C. for 16 hours; and
(g) cooling to room temperature in 1 hour.

After stripping, a plate was obtained from which test pieces of 30×7×4 mm size were cut and used for measuring the initial flexural characteristics (strength and modulus):

| | Flexural strength | |
|---|---|---|
| at 23° C. | 139 MPa | |
| at 250° C. | 73.5 MPa | |
| | Flexural modulus | |
| at 23° C. | 3387 MPa | |
| at 250° C. | 2762 MPa | |

EXAMPLE 8

An apparatus which consisted of a glass reactor, equipped with a central stirrer and a degassing tubulus connected to a vacuum pump through cold traps (a solid carbon dioxide +acetone mixture) was used.

The reactor was immersed in an oil bath heated to 160° C. The reactor was charged with:

(i) 90.25 g of N,N'-4,4'-diphenylmethane-bismaleimide;
(ii) 19.25 g of N-(4-allyloxyphenyl)maleimide; and
(iii) 37.50 g of diphenylsilanediol over the course of 3 minutes, under stirring.

This molten and homogeneous mixture was stirred for 26 minutes. The reaction mass was cooled to 120° C. in 10 minutes and degassed under reduced pressure (660 Pa) for 4 minutes.

Atmospheric pressure was then re-established in the reactor and 2.85 g of triallyl isocyanurate containing 0.15 g of imidazole were introduced.

The mixture was stirred for 1 minute, while maintaining the temperature at 120° C.; it was then degassed again under reduced pressure (400 Pa) for 3 minutes.

The reaction mass was stirred for an additional 5 minutes at 120° C. under atmospheric pressure and then cast in a mold which was pre-heated to 110° C. and which consisted of two rectangular chromium-plated plates separated by a 4 mm-thick air gap.

On another fraction of the composition, changes over time in dynamic viscosity at 90° C. (determined with a rotary bob viscometer) and its gel time at 160° C. were determined.

The polymerization of the resin contained in the mold was carried out at atmospheric pressure in an oven heated according to the following thermal cycle:

(a) temperature rise from 110° C. to 150° C. in 1 hour;
(b) maintenance at 150° C. for 1 hour;
(c) temperature rise from 150° C. to 200° C. in 1 hour; and
(d) maintenance at 200° C. for 1 hour.

At the end of this cycle, the resin was polymerized.

It was reheated (still in the mold) for 15 h, 30 min. in another oven at 250° C. It was permitted to cool to room temperature.

After stripping, a pale ochre-colored plate with no surface defects was obtained.

Test pieces of 30×7×4 mm size were cut from this plate and used for the determination of flexural characteristics (strength and modulus) before aging (initial values) and after 1000 hours at 250° C. in air.

The weight loss observed after this period of thermal aging was also determined on these test pieces.

Finally, the temperature at which the material began to decompose was determined by thermogravimetry at 5° C./minute in air using a test piece which was ground to a powder of particle size ≦ 100 μm.

(1) The characteristics measured on the unpolymerized resin were as follows:

| Dynamic viscosity at 90° C. | |
|---|---|
| time 0 | 5.28 Pa × s |
| after 1 hr at 90° C. | 12.4 Pa × s |
| after 2 hr at 90° C. | 28.8 Pa × s |
| Gel time at 160° C.: 10.4 minutes. | |

(2) Characteristics of the polymerized resin:
Temperature at beginning of decomposition: 344° C.
Flexural strength and flexural modulus:

| Flexural strength (in MPa) | | | |
|---|---|---|---|
| initial | | after 1000 hr at 250° C. | |
| at 23° C. | at 250° C. | at 23° C. | at 250° C. |
| 110 | 49 | 91 | 48 |

| Flexural modulus (in MPa) | | | |
|---|---|---|---|
| initial | | after 1000 hr at 250° C. | |
| at 23° C. | at 250° C. | at 23° C. | at 250° C. |
| 1950 | 1190 | 2700 | 1700 |

Weight loss after 1000 hr at 250° C. in air: 4.58%
No cracking of the test pieces thus aged.

EXAMPLE 9

Example 8 was repeated, substituted N-(4-allyloxyphenyl)maleimide with N-(3-allyloxyphenyl)maleimide.
(1) Characteristics of the unpolymerized resin:
Initial viscosity at 90° C.: 0.54 Pa×s
Gel time at 160° C.: 20.9 minutes.
(2) Characteristics of the polymerized resin:
Temperature at beginning of decomposition: 354° C.
Flexural strength and flexural modulus:

| Flexural strength (in MPa) | | | |
|---|---|---|---|
| initial | | after 1000 hr at 250° C. | |
| at 23° C. | at 250° C. | at 23° C. | at 250° C. |
| 100 | 47 | 106 | 56 |
| Flexural modulus (in MPa) | | | |

| -continued | | | |
|---|---|---|---|
| initial | | after 1000 hr at 250° C. | |
| at 23° C. | at 250° C. | at 23° C. | at 250° C. |
| 2000 | 1300 | 2500 | 1500 |

Weight loss after 1000 hr at 250° C. in air: 5.4%

EXAMPLE 10

The procedure of Example 8 was repeated, using the following charges:
(i) 85.0 g of N,N'-4,4'-diphenylmethane-bismaleimide;
(ii) 25.0 g of N-(3-allyloxyphenyl)maleimide; and
(iii) 12.5 g of diphenylsilanediol.
The molten mixture was stirred for 26 minutes.
The reaction mass was cooled to 120° C. over 10 minutes and degassed at 400 Pa for 4 minutes.
Atmospheric pressure has then re-established in the reactor and 2.375 g of triallyl isocyanurate, containing 0.125 g of imidazole, were introduced.
The mixture was stirred for 4 minutes at 135° C. and was then degassed again for 12 minutes at 930 Pa.
The amber-colored, homogeneous reaction mass was cast in the pre-heated mold described in Example 8 and polymerized as indicated in Example 8.
(1) Characteristics of the unpolymerized resin:
Initial viscosity at 90° C.: 0.4 Pa x s
Gel time at 160° C.: 34 minutes
(2) Characteristics of the polymerized resin:
Temperature at beginning of decomposition: 358° C.
Flexural strength and flexural modulus:

| Flexural strength (in MPa) | | | | Flexural modulus (in MPa) | | | |
|---|---|---|---|---|---|---|---|
| initial | | after 1000 hr at 250° C. | | initial | | after 1000 hr at 250° C. | |
| at 23° C. | at 250° C. | at 23° C. | at 250° C. | at 23° C. | at 250° C. | at 23° C. | at 250° C. |
| 138 | 76 | 126 | 59 | 3000 | 1900 | 3100 | 2600 |

Weight loss after 1000 hr at 250° C. in air: 3.85

EXAMPLE 11

The procedure of Example 8 was repeated, using the various reagents listed below:
(i) 90.0 g of N,N'-4,4'-diphenylmethane-bismaleimide;
(ii) 12.0 g of N,N'-1,3-(4-methylphenylene)-bismaleimide;
(iii) 15.0 g of diphenylsilanediol;
(iv) 30.0 g of N-(3-allyloxyphenyl)maleimide;
(v) 2.85 g of triallyl isocyanurate; and
(vi) 0.15 g of imidazole.
(1) Characteristics of the unpolymerized resin:
Initial dynamic viscosity at 90° C.: 0.82 Pa×s
Gel time at 160° C.: 30 minutes
(2) Characteristics of the polymerized resin:
Flexural strength and flexural modulus:

| Flexural strength (in MPa) | | | | Flexural modulus (in MPa) | | | |
|---|---|---|---|---|---|---|---|
| initial | | after 1000 hr at 250° C. | | initial | | after 1000 hr at 250° C. | |
| at 23° C. | at 250° C. | at 23° C. | at 250° C. | at 23° C. | at 250° C. | at 23° C. | at 250° C. |
| 136 | 74 | 135 | 49 | 3000 | 2100 | 3000 | 2300 |

Weight loss after 1000 hr at 250° C. in air: 3.68%

EXAMPLE 12

The apparatus described in Example 8 was charged with 18.78 g of N-(3-allyloxyphenyl)maleimide.
The reactor was immersed in an oil bath heated to 160° C. and 38.32 g of N,N'-4,4'-diphenylmethane-bismaleimide and 5.63 g of diphenylsilanediol were introduced, under stirring.
After 8 minutes, the mixture was molten and homogeneous.
The mixture was stirred for an additional 20 minutes at 160° C. and was then cooled to 120° C.
A degassing was carried out at a pressure of 400 Pa for 4 minutes.
After returning to atmospheric pressure, a mixture of:
(i) 0.036 g of imidazole;
(ii) 1.80 g of N,N',N''-tris(hydroxyethyl)hexahydrotriazine; and
(iii) 2.94 g of diallyl phthalate;
was added.
Degassing was carried out again at 1300 Pa for 4 minutes at 120° C.
A portion of the composition was cast in the mold described in Example 3 at 110° C. The resin contained in the mold was polymerized according to the thermal cycle indicated in Example 3.
(1) Characteristics of the unpolymerized resin:
Initial dynamic viscosity at 90° C.: 2.57 Pa×s
Dynamic viscosity after 2 hr at 90° C.: 4.54 Pa×s
(2) Characteristics of the polymerized resin:
Initial flexural strength at 23° C.: 137 MPa
Initial flexural strength at 250° C.: 53 MPa
Initial flexural modulus at 23° C.: 2700 MPa
Initial flexural modulus at 250° C.: 1200 MPa

EXAMPLE 13

Example 10 was repeated, substituting N-(3-allyloxyphenyl)maleimide with N-(2-allyloxyphenyl)maleimide.
The amounts of the different reagents used were as follows:
(i) 40.8 g of N,N'-4,4'-diphenylmethane-bismaleimide;
(ii) 12.0 g of N-(20-allyloxyphenyl)maleimide;
(iii) 6.0 g of diphenylsilanediol;
(iv) 1.14 g of triallyl isocyanurate; and
(v) 0.06 g of imidazole.
The composition obtained before polymerization was clear.
The polymerization in the mold described in Example 8 was carried out according to the thermal cycle indicated for the previous examples.
Characteristics of the polymerized resin:
Initial flexural strength at 23° C.: 162 MPa Initial flexural strength at 250° C.: 84 MPa
Initial flexural modulus at 23° C.: 3100 MPa
Initial flexural modulus at 250° C.: 2000 MPa

EXAMPLE 14

An apparatus which consisted of a glass reactor, equipped with a central stirrer and a degassing tubulus connected to a vacuum pump through cold traps (a solid carbon dioxide +acetone mixture) was used.

The reactor was immersed in an oil bath heated to 160° C. The reactor was charged with:
(i) 67.2 g of N,N'-4,4'-diphenylmethane-bismaleimide;
(ii) 20.98 g of N-(4-methallyloxyphenyl)maleimide; and
(iii) 9.82 g of diphenylsilanediol; over the course of 3 minutes, under stirring.

This molten and homogeneous mixture was stirred for 26 minutes. The reaction mass was cooled to 120° C. over 10 minutes and degassed under reduced pressure (660 Pa) for 4 minutes.

Atmospheric pressure was then re-established in the reactor and 2.0 g of triallyl isocyanurate, containing 0.10 g of imidazole, were introduced.

The mixture was stirred for 1 minute, while maintaining the temperature at 120° C.; it was then degassed again under reduced pressure (400 Pa) for 3 minutes.

The reaction mass was stirred for an additional 5 minutes at 120° C. at atmospheric pressure and then cast in a mold which was pre-heated to 110° C. and was made of two rectangular chromium-plated plates separated by a 4 mm-thick air gap.

On another fraction of the compositions: changes with time in the dynamic viscosity at 90° C. (determined using a rotary bob viscometer) and its gel time at 160° C. were determined.

The polymerization of the resin contained in the mold was carried out at atmospheric pressure, in an oven heated according to the thermal cycle below:
(a) temperature rise from 100° C. to 150° C. in 1 hour;
(b) maintenance at 150° C. for 1 hour;
(c) temperature rise from 150° C. to 200° C. in 1 hour;
(d) maintenance at 200° C. for 1 hour.

At the end of the cycle, the resin was polymerized.

It was reheated (still in the mold) for 15 hr, 30 min, in another oven at 250° C. It was permitted to cool to room temperature. After stripping, a pale ochre-colored plate with no surface defects was obtained.

Test pieces of 30×7×4 mm size were cut from this plate and used for the determination of flexural characteristics (strength and modulus).

Finally, the temperature at which the material began to decompose was determined by thermogravimetry at 5° C./minute in air, using a test piece which was ground into a powder of particle size <100 μm.

(1) Characteristics of the unpolymerized resin:
Dynamic viscosity at 90° C.: time 0: 226 Pa×s
Dynamic viscosity after 1 hr at 90° C.: 386 Pa×s
Gel time at 160° C.: 13.8 minutes
(2) Characteristics of the polymerized resin:
Temperature at beginning of decomposition: 360° C.
Flexural strength and flexural modulus:
Initial flexural strength at 23° C.: 113 MPa
Initial flexural strength at 250° C.: 72 MPa
Initial flexural modulus at 23° C.: 2470 MPa
Initial flexural modulus at 250° C.: 1820 MPa

EXAMPLE 15

Example 14 was repeated, substituting N-(4methallyloxyphenyl)maleimide with N-(3-methallyloxyphenyl)maleimide.

After stripping, a pale ochre-colored plate was obtained.
(1) Characteristics of the unpolymerized resin:
Dynamic viscosity at 90° C.: time 0: 7.9 Pa×s
Gel time at 160° C.: 23.4 minutes
(2) Characteristics of the polymerized resin:
Temperature at beginning of decomposition: 360° C.
Flexural strength and flexural modulus:
Initial flexural strength at 23° C.: 122 MPa
Initial flexural strength at 250° C.: 67 MPa
Initial flexural modulus at 23° C.: 2400 MPa
Initial flexural modulus at 250° C.: 1890 MPa

EXAMPLE 16

Example 14 was repeated, substituting N-(4-methallyloxyphenyl)maleimide with N-(2-methallyloxyphenyl)maleimide.

After stripping, a dark red, transparent plate was obtained.
(1) Characteristics of the unpolymerized resin:
Dynamic viscosity at 90° C.: time 0: 8.2 Pa×s
Gel time at 160° C.: 19.5 minutes
(2) Characteristics of the polymerized resin:
Temperature at beginning of decomposition: 363° C.
Flexural strength and flexural modulus:
Initial flexural strength at 23° C.: 1400 MPa
Initial flexural strength at 250° C.: 67 MPa
Initial flexural modulus at 23° C.: 2530 MPa
Initial flexural modulus at 250° C.: 1800 MPa While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A thermosetting composition of matter comprising (A) a prepolymer of (a) at least one bis-imide having the general formula (II):

$$\begin{array}{c} YC-CO \\ \| \\ YC-CO \end{array} N-L-N \begin{array}{c} CO-CY \\ \| \\ CO-CY \end{array} \quad (II)$$

wherein Y is hydrogen or methyl; L is a divalent hydrocarbon radical or a radical having the formula (III):

$$\begin{array}{c} X \\ \end{array} \begin{array}{c} X \\ \end{array} \quad (III)$$

in which T is a valence bond or T represents one of the following:

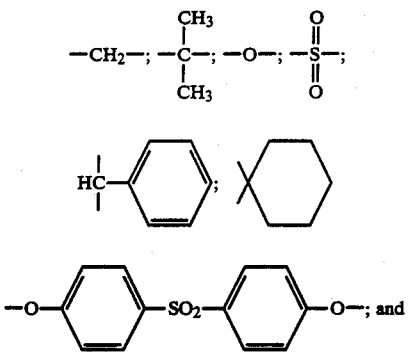

X is hydrogen, methyl, ethyl or isopropyl, with (b) at least one monomaleimide having the following general formula (I):

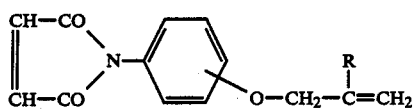

wherein R is hydrogen or methyl; and (B) at least one imidazole compound.

2. The thermosetting composition as defined by claim 1, said prepolymer further comprising (c) at least one organosilicic compound having at least one hydroxyl group bonded to a silicon atom in the molecular structure thereof.

3. The thermosetting composition as defined by claim 1, wherein L is cyclohexylene, phenylene, 4-methyl-1,3-phenylene, 2-methyl-1,3-phenylene, 5-methyl-1,3-phenylene or 2,5-dimethyl-3-methyl-1,4-phenylene.

4. The thermosetting composition as defined by claim 1, said at least one bis-imide (II) comprising
N,N'-meta-phenylene-bis-maleimide;
N,N'-para-phenylene-bis-maleimide;
N,N'-4,4'-diphenylmethane-bis-maleimide;
N,N'-4,4'-diphenylether-bis-maleimide;
N,N'-4,4'-diphenylsulfone-bis-maleimide;
N,N'-1,4-cyclohexylene-bis-maleimide;
N,N'-4,4'-(1,1-diphenylcyclohexylidene)bismaleimide;
N,N'-4,4'-(2,2-diphenylpropane)bis-maleimide;
N,N'-4,4'-triphenylmethane-bis-maleimide;
N,N'-1,3-(4-methylphenylene)bis-maleimide; or
N,N'-1,3-(2-methylphenylene)bis-maleimide.

5. The thermosetting composition as defined by claim 4, said at least one monomaleimide (b) comprising
N-(2-allyloxyphenyl)maleimide;
N-(3-allyloxyphenyl)maleimide;
N-(4-allyloxyphenyl)maleimide;
N-(2-methallyloxyphenyl)maleimide;
N-(3-methallyloxyphenyl)maleimide;
N-(4-methallyloxyphenyl)maleimide;
or admixture thereof.

6. The thermosetting composition as defined by claim 2, said at least one organosilicic compound (c) having the general formula (IV):

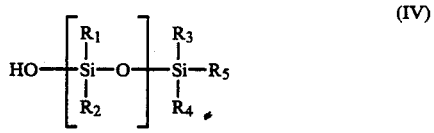

in which $R_1$, $R_2$, $R_3$, $R_4$ and $R_5$, which are identical or different, are each hydroxyl or $-OR_6$ in which $R_6$ is a straight or branched chain alkyl radical containing 1 to 6 carbon atoms or a phenyl radical; hydrogen; a straight or branched chain alkyl radical containing 1 to 6 carbon atoms or a substituted such radical bearing one or more chlorine, fluorine or $-CN$ substituents; a straight or branched chain alkenyl radical containing 2 to 6 carbon atoms; a phenyl radical, or a substituted phenyl radical bearing at least one of alkyl and alkoxy substituents containing 1 to 4 carbon atoms, or one or more chlorine atoms; and y is an integer or a fractional number ranging from 0 to 1000.

7. The thermosetting composition as defined by claim 1, said at least one imidazole compound (B) having the general formula (V):

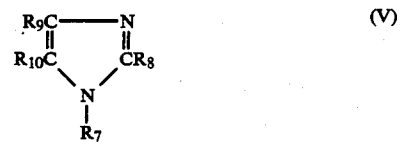

In which $R_7$, $R_8$, $R_9$ and $R_{10}$, which are identical or different, are each a hydrogen atom, an alkyl or alkoxy radical containing 1 to 20 carbon atoms, a vinyl radical, a phenyl radical, or a nitro group, or $R_9$ together forms, with $R_{10}$ and the carbon atoms to which $R_9$ and $R_{10}$ are linked, a single hydrocarbon ring, or $R_7$ is a carbonyl group linked to a second imidazole ring.

8. The thermosetting composition as defined by claim 1, said at least one bis-imide (II) comprising N,N'-4,4'-diphenylmethane-bis-maleimide, N,N'-1,3-(4-methylphenylene)-bis-maleimide, N,N'-1,3-(2-methylphenylene)-bismaleimide, or admixture thereof.

9. The thermosetting composition as defined by claim 2, said at least one organosilicic compound (c) comprising diphenylsilanediol.

10. The thermosetting composition as defined by claim 1, comprising from 50 to 95% by weight of said at least one bis-imide (II) and from 5 to 50% by weight of said at least one monomaleimide (b).

11. The thermosetting composition as defined by claim 2, comprising from 40 to 90% by weight of said at least one bis-imide (II), from 5 to 40% by weight of said at least one monomaleimide (b), and from 5 to 40% by weight of said at least one hydroxylated organosilicic compound (c).

12. The thermosetting composition as defined by claim 1, comprising from 0.02 to 1% by weight of said at least one imidazole compound (B).

13. The thermosetting composition as defined by claim 1, further comprising up to 5% by weight of an N,N',N''-tris(hydroxyalkyl)hexahydrotriazine, relative to said prepolymer (A).

14. A process for the preparation of the thermosetting composition as defined by claim 1, comprising (i) intimately admixing the maleimido compounds, (ii) melting said admixture at a temperature not exceeding the melting point of the most difficult to liquefy of said maleimides, (iii) adding a solvent solution of said at least one imidazole compound thereto, under vigorous stirring, (iv) degassing the resulting mixture, (v) homogenizing same, and (vi) casting the resin immediately thereafter.

15. A cured composition produced from the thermosetting composition as defined by claim 1.

16. A shaped article comprising the cured composition as defined by claim 15.

* * * * *